United States Patent
Cappa et al.

(10) Patent No.: US 6,241,865 B1
(45) Date of Patent: Jun. 5, 2001

(54) SENSOR FOR THE MEASUREMENT OF GAS CONCENTRATIONS

(75) Inventors: Guido Cappa, Houthalen; Paul Jacobs, Lokeren; Peter van Geloven, Holsbeek, all of (BE)

(73) Assignee: Heraeus Holding GmbH (DE)

( * ) Notice: Subject to any disclaimer, the term of this patent is extended or adjusted under 35 U.S.C. 154(b) by 0 days.

(21) Appl. No.: 09/152,396

(22) Filed: Sep. 14, 1998

(30) Foreign Application Priority Data

Sep. 15, 1997 (DE) ............................................. 197 40 503
Oct. 7, 1997 (DE) ............................................. 197 44 224

(51) Int. Cl.⁷ .................................................. G01N 27/407

(52) U.S. Cl. ........................... 204/427; 204/408; 204/424

(58) Field of Search ............................. 204/408, 421–429

(56) References Cited

U.S. PATENT DOCUMENTS

| | | |
|---|---|---|
| 4,075,968 | 2/1978 | Caddock . |
| 4,123,344 * | 10/1978 | Davis ................... 204/426 |
| 4,400,260 | 8/1983 | Stahl . |
| 4,502,939 * | 3/1985 | Holfelder et al. ............ 204/425 |
| 4,629,549 * | 12/1986 | Kojima et al. ............ 204/425 |
| 4,639,305 | 1/1987 | Shibata . |
| 4,776,943 * | 10/1988 | Kitahara ................... 204/426 |
| 4,980,042 | 12/1990 | Shiomi . |
| 5,139,829 | 8/1992 | Minoha . |
| 5,342,498 * | 8/1994 | Graves et al. ............ 204/408 |
| 5,895,591 * | 4/1999 | Kojima et al. ............ 204/426 |
| 5,935,399 * | 8/1999 | Tanaka et al. ............ 204/425 |

FOREIGN PATENT DOCUMENTS

| | | |
|---|---|---|
| 32 25 483 A1 | 5/1983 | (DE) . |
| 30 35 608 C2 | 12/1988 | (DE) . |
| 36 28 572 C2 | 8/1990 | (DE) . |
| 195 34 918 A1 | 1/1997 | (DE) . |
| 197 03 636 A1 | 1/1997 | (DE) . |
| 44 01 793 C2 | 2/1997 | (DE) . |
| 196 46 013 A1 | 5/1997 | (DE) . |
| 197 03 636 A1 | 8/1997 | (DE) . |
| 0 125 069 | 4/1984 | (EP) . |
| 0 501 593 A2 | 9/1992 | (EP) . |
| 10-010081 | 1/1998 | (JP) . |

* cited by examiner

Primary Examiner—T. Tung
(74) Attorney, Agent, or Firm—George H. Gerstman; William J. Hallihan; Seyfarth Shaw

(57) ABSTRACT

The invention relates to a sensor for the measurement of gas concentrations in a gas mixture, comprising a ceramic sensor tube that is closed at one end, arranged in a casing, and exhibits an outer surface which consists at least partially of a solid electrolyte material, and with at least one sensor contact and at least one heating contact with an active heating surface arranged along its exterior. To provide a gas sensor with a short response time that continues to operate precisely and with long-term stability in hot exhaust gases, sensor contacts are screen-printed onto the sensor tube, where at least the active heating surface is arranged in rotational symmetry around the perimeter of the sensor tube and where the heating contact is arranged on an electrically insulating layer applied to the solid electrolyte material in such a way that it does not cover the sensor contact, of which there is at least one.

14 Claims, 2 Drawing Sheets

SENSOR FOR THE MEASUREMENT OF GAS CONCENTRATIONS

FIELD OF THE INVENTION

The invention relates to a sensor for the measurement of gas concentrations in a gas mixture, comprising a ceramic sensor tube that is closed at one end, arranged in a casing, and exhibits an outer surface which consists at least partially of a solid electrolyte material, and with at least one sensor contact and at least one heating contact with an active heating surface arranged along its exterior. In addition, the invention relates to a process for the manufacture of the sensor.

BACKGROUND OF THE INVENTION

This type of sensor is known from DE-A-195 34 918. In the sensor described here, several sensor contacts are arranged next to a heating contact on a solid electrolyte tube. The arrangement disclosed here is well-suited for heating output in the middle or lower range, with the heater producing a gradual heating effect. If the sensor tube is heated unevenly, the thermomechanical tension may result in the destruction of the tube or may cause the contact surfaces to become detached from the sensor tube. The same type of sensor is known from DE-C-30 35 608; in this case, however, a wire-shaped heater is coiled on the sensor surface. A heater contact is fed through the inside of the sensor tube. In order to ensure a uniform grip on the sensor surface and to contact or feed the wire along the inside of the sensor tube, this type of arrangement must be relatively complicated, as such features may result in sealing problems at the point at which the wire is fed through the sensor material.

The use of tampon pressure to apply sensor contacts (external electrodes) to a cylindrical sensor object is known from DE-A-32 25 483. However, because of the relatively soft color transfer elements, tampon pressure is relatively inaccurate and completely unsuited for use in such devices as heater structures. Heater structures, such as those known from DE 195 34 918, produce uncontrolled temperature behavior at even minor dimensional variances because variances from the predetermined surface lead directly to variances in resistance.

In a sensor arrangement known from DE-C-36 28 572, the cap of the sensor tube is made of solid electrolyte material and a heater is arranged on an insulating material on the surface of the casing. These varying sensor surface structures produce the thermomechanical tension described in the published application, thereby creating the risk of destruction of the sensor.

A completely different sensor design is known from DE-C-44 01 793 or from DE-A-196 46 013. In this sensor design, a heating rod is arranged inside the sensor tube. The surface of the sensor tube is heated by thermal conduction beginning at the heating rod and passing through the atmosphere inside the sensor tube and through the sensor tube itself until the heat reaches the sensor external surface. Thus, this type of heating system is relatively sluggish. Because of the high thermal resistance between the sensor surface and the heater, it is impossible to precisely regulate the temperature of the sensor surface where the active sensor contacts (sensor electrodes) are located. Furthermore, if the position of the heating rod is not rotationally symmetrical inside the sensor tube, this sensor tube may be heated unevenly. The advantage of this arrangement, however, is that inaccuracies that occur when the heating conductor is pressed against the heating rod according to the procedure described in DE-A-32 25 483 are relatively unproblematic, as the heating rod itself is solid and thus relatively stable. Consequently, any inhomogeneous heating of the surface of the heating rod caused by the required thermal conduction to the surface of the sensor tube does not lead to an analogous inhomogeneity in the heating of the surface of the sensor tube.

The use of various processes to coat cylindrical substrates is also known in the art. For example, the use of screen printing to apply resistor layers of cylindrical layered resistors is known from EP-A-501 593 or from U.S. Pat. No. 4,075,968, where the resistance value itself is determined by the Greek key-shaped layers. The inhomogeneous distribution of the resistor layers on the substrates is not critical in these resistors, as such resistors exhibit low temperatures of about 100°, so that thermomechanical tension inside the substrate material is virtually nonexistent.

A lambda sensor is known from DE-A1-197 03 636 which comprises a sensor tube with a sensor contact arranged along its exterior and a layer of insulation positioned above the sensor contact; a heating contact is positioned on the insulation layer above the sensor contact. This arrangement is designed to achieve rapid heating of the sensor, thus ensuring that the sensor can become operational without a delay and can measure exhaust gas concentrations in motor vehicles when the exhaust gas is still cold. However, the disadvantage of this arrangement is that the gas to be measured comes into contact with the metallic heater before it reaches the sensor contact. When this occurs, the gas to be measured reacts with the metallic heater and does not reach the sensor contact in an unadulterated state. Consequently, the result of the measurement does not reflect actual conditions in the gas.

Based on the known state of the art, the objective of the invention is to provide a gas sensor that exhibits a short response time and that continues to operate precisely and with long-term stability in hot exhaust gases. In addition, the objective of the invention is to describe a process for the manufacture of this type of sensor.

SUMMARY OF THE INVENTION

In accordance with the present invention, the sensor contact and the heating contact are screen-printed onto the sensor tube, with at least the active heating surface rotationally symmetrical around the perimeter of the sensor tube, and with the heating contact arranged in such a way on an electrically insulating layer applied to the solid electrolyte material that it does not cover the sensor contact, of which there is at least one. Thus, it is arranged along the perimeter of the sensor next to the sensor contact, of which there is at least one. It has been demonstrated that this type of sensor can be heated very precisely and evenly, and that it operates without difficulty in the 400° C. to 1000° C. temperatures commonly found in motor vehicle exhaust gases. The rotationally symmetrical design of the heating contact prevents thermomechanical tension from occurring in the material of the relatively thin sensor tube, which might otherwise be destroyed by such tension. Furthermore, temperature fluctuations, such as those that occur at the sensor surface when the exhaust gas velocity in motor vehicles fluctuates, can be avoided. Even at high operating temperatures, the screen printing process yields exactly adhering, geometrically precise contacts, thus allowing for the precise determination of heat output.

The heating contact and/or sensor contact is preferably arranged on the sensor tube in a Greek key pattern, with the Greek key pattern continuing around the perimeter of the sensor tube. This allows for very uniform placement of the contacts and, consequently, very uniform warming of the sensor tube. It is especially advantageous if the Greek key pattern of the heater consists of segments running alternately in the axial and the circumferential directions of the sensor tubes, with the width of the active heating surfaces that run in the axial direction being smaller than the width of the active heating surfaces that run in the circumferential direction. Furthermore, it is advantageous if the rotational symmetry is dyadic to decadic, especially quadratic, as this results in a more homogenous sensor arrangement (e.g., in relation to the heating process) while retaining a simple design. The sensor contact, of which there is at least one, can be fully or partially arranged on the solid electrolyte material or on an electrically insulating material, especially on an electrically insulating layer applied to the solid electrolyte material (insulating layer). This allows for the development of both resistive and potentiometric or amperometric sensors. The electrically insulating layer is preferably made of aluminum oxide or spinel, i.e., of materials that are relatively easy to apply, while at the same time exhibiting the necessary temperature resistance and chemical endurance.

The sensor tube can consist of a basic body made of a high-temperature resistant material, such as spinel or aluminum oxide, on which the solid electrolyte material, such as zirconium oxide, is arranged. The sensor tube can also consist entirely of the solid electrolyte material. The objective of manufacturing the sensor according to the invention in a process according to the invention is solved in that both the sensor contact and the heating contact are applied to the ceramic sensor tube by means of a screen printing process. It has proven to be advantageous to print the heating contact and the sensor contact in sequence, especially if the heating contact can be printed first. However, it can be advantageous to print the heating contact and the sensor contact at the same time. In this case, the electrically insulating layer needed for the heating contact must include recesses into which the sensor contact can be placed and arranged directly on the solid electrolyte material of the sensor tube, unless it is also placed onto an insulating layer. The electrically insulating layer (insulating layer) can also, and preferably, be screen printed.

In the following text, an illustrative embodiment of the invention is described in greater detail on the basis of the drawings.

DETAILED DESCRIPTION OF THE ILLUSTRATIVE EMBODIMENT

Figure 1:
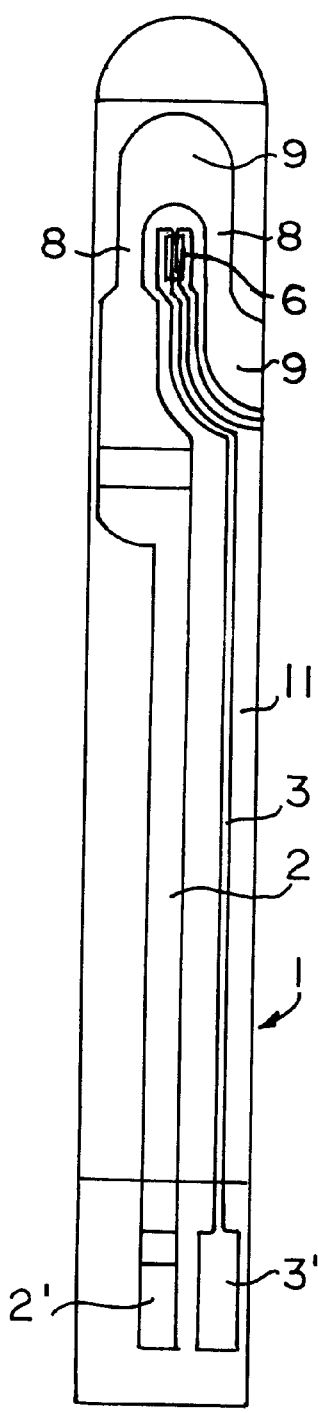
FIG. 1 depicts a view of the sensor tube.
Figure 2:
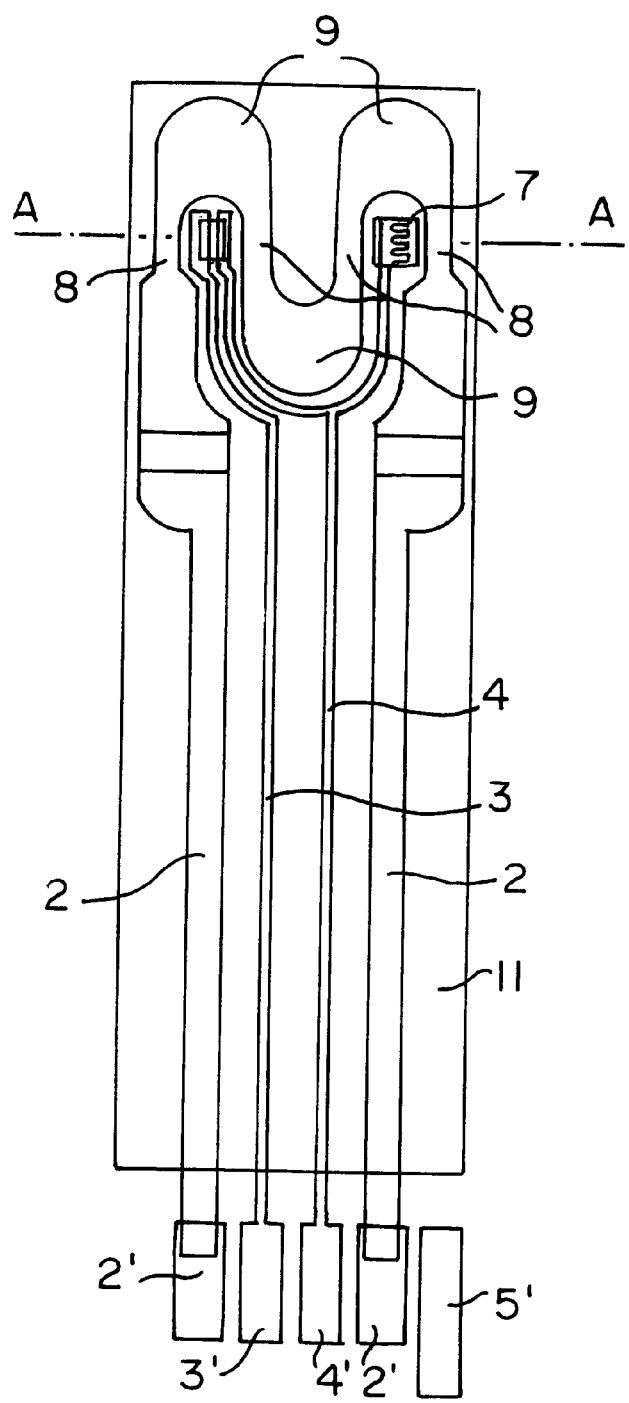
FIG. 2 depicts a view of the surface shell of the sensor.

FIG. 1 provides a schematic depiction of the sensor tube of the sensor according to the invention. The sensor tube can be arranged and bonded in a manner known to a person skilled in the art. Such casings are, for example, known from and described in detail in DE-A1-197 03 636. The sensor tube 1 exhibits a heating contact 2 and several sensor contacts 3, 4. The contacts 2, 3, 4 run essentially along the sensor tube 1. They include contact surfaces 2', 3', 4' at the open end of the sensor tube 1 which provide for electrical contacting of the sensor tube 1 (also see FIG. 2). In the cross-sectional depiction shown in FIG. 3, an internal electrode 5 arranged inside the sensor tube 1 includes a connection surface 5' at the open end of the sensor the sensor tube.

The sensor tube 1 is closed at one end and includes zirconium oxide as a solid matter electrolyte 10. It can consist entirely of zirconium oxide or can only include zirconium oxide on those portions of its surface onto which the active sensor surfaces 6, 7 are arranged. The sensor contacts 3, 4 include active sensor surfaces 6, 7 at their ends facing the closed end of the sensor tube 1. Thus, in addition to the strip conductors running alongside the sensor tube 1, the sensor contacts 3, 4 also encompass the contact surfaces 3', 4' and the active sensor surfaces 6, 7. The heating contact 2 includes active heating surfaces 8 in direct proximity to the active sensor surfaces 6, 7. The cross-section of these active heating surfaces 8 is smaller than that of the heating contacts 2 in the adjacent areas 9. Thus, in addition to the strip conductors running alongside the sensor tube 1, the heating contact 2 also encompasses the contact surface 2', the active heating surface 8 and the adjacent areas 9. The resistance of the heating contact is substantially lower in the adjacent areas 9, so that these surfaces are not heated nearly as intensively as the active heating surfaces 8. The active heating surfaces 8 are arranged in rotational symmetry next to the active sensor surfaces 6, 7 in the circumferential direction of the sensor tube 1. This allows for a favorable thermal connection between the heating contact 2 with its active heating surfaces 8 and the sensor contacts 3, 4, which results in the rapid heating of the active sensor surfaces 6, 7. At the same time, the entire sensor tube 1 is heated uniformly, thus avoiding tensions inside the sensor material that could result in the destruction of the sensor tube 1.

The heating contact 2 is applied to an insulating layer 11 arranged on the solid electrolyte 10 of the sensor tube 1. The insulating layer 11 may, for example, consist of aluminum oxide.

Figure 3:
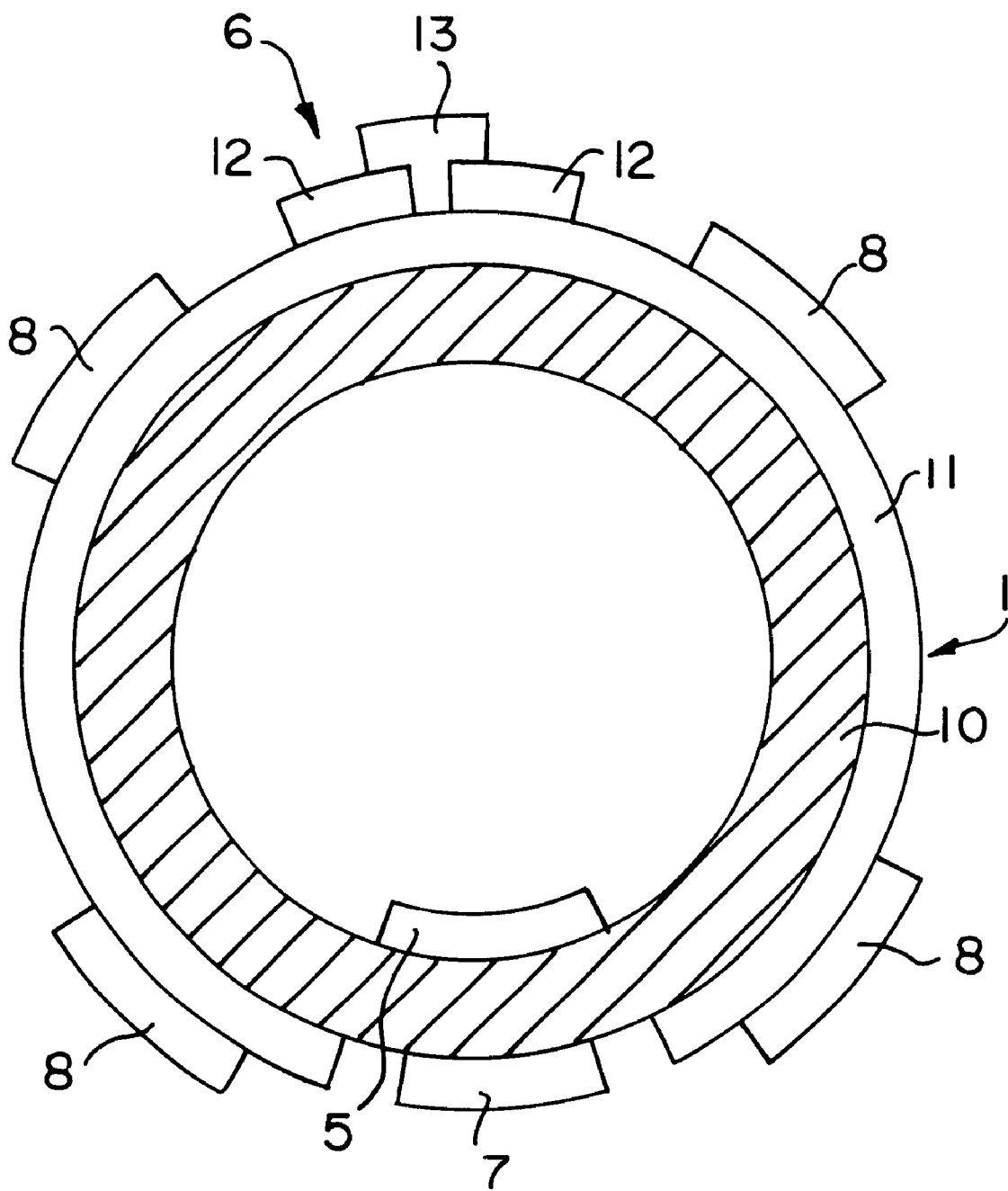
FIG. 3 depicts a sectional view of the sensor.

The sensor contacts 3, 4 with their active sensor surfaces 6, 7 can be constructed in different ways. For example, the active sensor surface 7 can be arranged directly on the solid electrolyte 10, i.e., it can contact the electrolyte electrically and form a measuring circuit with the interior electrode 5 to test a portion of the gas mixture surrounding the sensor, while the second active sensor surface 6 can be arranged on the insulating layer 11, i.e., not touching the solid electrolyte 10. The insulating layer 11 can be applied by means of screen printing. FIG. 3 (sensor cross-section along line A—A in FIG. 2) depicts this type of arrangement with two different sensor contacts 3, 4 and the corresponding differently-shaped active sensor surfaces 6, 7. The second active sensor surface 6 comprises two sensor electrodes 12 and an active sensor material 13 connecting the two sensor electrodes 12. The sensor electrodes 12 may, for example, consist of platinum or gold. The active sensor material 13 can serve as a solid electrolyte and may consist of zirconium oxide; if the sensor is designed to act as a resistant sensor, it may consist of stannous oxide, strontium titanate or titanium oxide. The active sensor surface 6 with the active sensor material 13 is used to measure hydrocarbons, carbon monoxide or nitrous oxides.

The active sensor surface 7 may, for example, consist of platinum or a mixture or platinum and zirconium oxide, and is used to measure oxygen.

The entire sensor tube 1, including the sensor contacts 3, 4 and the heating contact 2 can be enveloped by a porous protective coating made of an inert material, such as aluminum oxide or spinel. In this interest of simplicity, this protective coating is not shown in the figures.

Both the structure of the heating contact 2 and the structure of the sensor contacts 3, 4 are screen-printed. The process of screen-printing heating contacts is known to a person skilled in the art, e.g., from DE-A-197 03 636. The sequence of screen printing the various layers 2, 3, 4, 6, 7, 11, 12, 13 depends mainly on the selection of materials for the layers, with the materials with the higher sintering temperatures being printed, dried and sintered first. Prior to screen printing, the solid electrolyte 10 is coated with an insulating layer, which is not applied to the position where the sensor contact is directly applied to the solid electrolyte 10. After screen printing, a porous protective coating is finally applied to the entire sensor tube, including the contacts 2, 3, 4.

Although an illustrative embodiment of the invention has been shown and described, it is to be understood that various modifications and substitutions may be made by those skilled in the art without departing from the novel spirit and scope of the present invention.

What is claimed is:

1. A sensor for the measurement of gas concentrations in a gas mixture comprising:
   a ceramic sensor tube that is closed at one end and has an outer surface which consists at least partially of a solid electrolyte material;
   at least one sensor contact;
   at least one heating contact on an electrically insulating layer applied to the solid electrolyte material, wherein the heating contact does not cover the sensor contact; and
   an active heating surface that is rotationally symmetrical around the perimeter of the sensor tube, wherein the heating contact is arranged in a serpentine pattern that runs in a circumferential direction around the sensor tube, the serpentine pattern comprises segments running alternately in the axial direction and in the circumferential direction of the sensor tube and the width of the active heating surfaces that run in the axial direction being smaller than the width of the active heating surfaces that run in the circumferential direction.

2. A sensor according to claim 1 wherein the sensor tube comprises a body of a high-temperature resistant material selected from the group consisting of spinel and aluminum oxide on which the solid electrolyte material is arranged.

3. A sensor according to claim 1 wherein the sensor tube is made entirely of solid electrolyte material.

4. A sensor according to claim 1 wherein the rotational symmetry is dyadic to decadic.

5. A sensor according to claim 1 wherein the rotational symmetry is quadratic.

6. A sensor according to claim 1 wherein the sensor contact is at least partially arranged on the solid electrolyte material.

7. A sensor according to claim 1 wherein the sensor contact is at least partially arranged on electrically insulating material.

8. A sensor according to claim 1 wherein the sensor contact is on the electrically insulating layer applied to the solid electrolyte material.

9. A sensor according to claim 1 wherein the electrically insulating layer is selected from the group consisting of aluminum oxide or spinel.

10. A sensor according to claim 1 wherein the serpentine pattern is a curved pattern.

11. A sensor according to claim 1 wherein the cross-sectional area of the active heating surfaces that run in the axial direction is smaller than the cross-sectional area of the active heating surfaces that run in the circumferential direction.

12. A sensor for the measurement of gas concentrations in a gas mixture comprising:
    a ceramic sensor tube that is closed at one end and has an outer surface which consists at least partially of a solid electrolyte material;
    at least one sensor contact;
    at least one heating contact on an electrically insulating layer applied to the solid electrolyte material such that the heating contact does not cover the sensor contact;
    an active heating surface that is symmetrical around the perimeter of the sensor tube; and
    wherein the active heating surface comprises segments running alternately in the axial direction and in the circumferential direction of the sensor tube, the width of the active heating surfaces that run in the axial direction of the sensor tube is smaller than the width of the active heating surfaces that run in the circumferential direction of the tube, and a portion of the sensor contact is positioned between two active heating surfaces that run in the axial direction.

13. A sensor according to claim 12 wherein the cross-sectional area of the active heating surfaces that run in the axial direction is smaller than the cross-sectional area of the active heating surfaces that run in the circumferential direction.

14. A sensor for the measurement of gas concentrations in a gas mixture comprising:
    a ceramic sensor tube that is closed at one end and has an outer surface which consists at least partially of a solid electrolyte material;
    at least one sensor contact;
    at least one heating contact on an electrically insulating layer applied to the solid electrolyte material such that the heating contact does not cover the sensor contact;
    an active heating surface that is radially symmetrical around the perimeter of the sensor tube; and
    wherein the active heating surface comprises segments running alternately in the axial direction and in the circumferential direction of the sensor tube, the width of the active heating surfaces that run in the axial direction of the sensor tube is smaller than the width of the active heating surfaces that run in the circumferential direction of the tube, and a portion of the sensor contact is positioned between two active heating surfaces that run in the axial direction.

\* \* \* \* \*